United States Patent [19]

Viherkoski

[11] Patent Number: 4,852,115
[45] Date of Patent: Jul. 25, 1989

[54] LASER HEAD

[76] Inventor: Esa Viherkoski, Lepolantie 21, SF-00660 Helsinki, Finland

[21] Appl. No.: 38,629

[22] Filed: Apr. 14, 1987

[30] Foreign Application Priority Data

Dec. 5, 1986 [FI] Finland .................................. 864969

[51] Int. Cl.$^4$ .............................................. H01S 3/08
[52] U.S. Cl. ........................................ 372/92; 372/99; 372/108
[58] Field of Search ....................... 372/92, 99, 41, 98, 372/108

[56] References Cited

U.S. PATENT DOCUMENTS

| 3,573,656 | 4/1971 | Marcatili | 372/99 |
| 3,736,040 | 5/1973 | Zivi et al. | 372/99 |
| 4,338,578 | 7/1982 | Sukhman | 372/29 |
| 4,589,118 | 5/1986 | Suzuki et al. | 372/41 |

OTHER PUBLICATIONS

Bethea; "Megawatt Power at 1.318μ in No.+3:YAG and Simultaneous Oscillation at Both 1.06 and 1.318μ", IEEEJQE Feb. 73, p. 254.

Primary Examiner—Léon Scott, Jr.
Attorney, Agent, or Firm—Merchant, Gould, Smith, Edell, Welter & Schmidt

[57] ABSTRACT

A laser head comprising a laser resonator (1) at least two pairs of front and rear mirrors (3, 4; 3$^1$, 4$^1$) which are similar, two and two, in their dielectric laser light transmitting, respectively reflecting, properties regardig the wavelength of the laser light which they transmit, respectively reflect, and that said first front and rear mirrors are exchangeable against said latter front and rear mirrors.

5 Claims, 1 Drawing Sheet

LASER HEAD

BACKGROUND OF THE INVENTION

The present invention concerns a laser head comprising a laser resonator which comprises a laser source, such as a laser crystal or rod, and a front and a rear mirror. In particular, the invention concerns a laser head chiefly intended for surgical purposes.

Laser apparatus used in surgery are in general provided with one laser head per unit. The first combination apparatus comprising two laser heads was an argon-crypton ophthalmic surgery laser which was developed in 1972 and in which were combined the blue-green wavelength of the argon laser and the red wavelength of the crypton laser in one single apparatus for treating different diseases, for instance for treating fundus of the eye in diabetics, for fixing a detached retina (argon laser), and degeneration of the macular area (krypton laser).

In the field of surgical universal lasers as rule a carbon dioxide laser ($CO_2$) of a YAG laser (Nd:YAG) has been used either for vaporizing or coagulating cell tissue. Depending on the application and on the user's economic recources, usually one or the other has been purchased: formerly (1950-1985) the $CO_2$ laser, nowadays often also the Nd:YAG laser.

As various laser apparatus applications are continuously increasing, and the need for using laser waves of different wavelengths is correspondingly increasing, the purchasing of different laser apparatus is problematic owing to the frequently high price of laser apparatus. Therefore, the lack of laser apparatus appropriate for different wavelength ranges constitutes a drawback which no one has been able to eliminate so far.

SUMMARY OF THE INVENTION

An object of the present invention is to eliminate the drawback mentioned. It is furthermore an object of the invention to provide a laser head specifically for surgical uses by which it is possible to produce laser beams with different wavelengths and which is usable in various surgical interventions which imply different wavelengths.

Concerning the characteristic features of the present invention reference is made to the claims below.

The invention is based on a novel laser head design in which the front and rear mirrors of the laser head can be exchanged against other front and rear mirrors so that from the laser head is obtained laser light of different wavelengths, depending on the mirrors used.

In the laser head, the laser light source usually emits several different wavelengths. When a rear mirror and a front mirror reflecting laser light of a given wavelength is used (part of the laser light of said wavelength being transmitted by the latter), the light of undesirable wavelength ranges can be filtered off and, as the front mirror passes only the desired laser light precisely in the desired wavelength range, said laser light of the desired wavelength leaves the tube through the front mirror in the well-known manner. The reflection characteristics of a laser mirror, that is, which the mirror will reflect, depend on the number and kind of the dielectric films provided on the surface of the laser mirror. In the design of the invention, specifically said front and rear mirrors of the laser head can be so replaced that the wavelength of the laser light emitted by the laser head can be changed to be as desired.

The laser mirrors to be used, their design and their placement in relation to the laser source are in themselves known in the art, and they will not be described more closely in the present context.

The laser mirrors are exchangeable against others, appropriately, with the aid of a special operating means, and the mirrors may be mounted for instance to be carried on a guide or in a special rotatable operating means of revolver type, or another equivalent shifting means.

The laser source to be used is such that it emits desire wavelengths so that it is possible by changing mirrors to select the desired wavelength. The laser sources to be potentially used in the laser head of the invention may be of any type, as is known in the art, for instance a Nd-YAG, Er-YAG, $CO_2$, CO, Ar, Kr, etc. laser source. Furthermore, the laser head may also include more than one laser source, e.g. two or even more sources, such as an Nd:YAG laser source and an Er:YAG laser source, of which only one at a time is used. Furthermore, the laser source, or laser sources when there are several, may emit continuous or pulsed laser light.

In an advantageous embodiment of the invention, the laser head may comprise a special wavelength-halving means, or frequency doubler, which is placed or disposed in the path of the laser beam in order to halve the laser beam's wavelength. Said wavelength halving means may be any KTP, KDP, KD*P, ADP or equivalent crystal or other laser light wavelength halving means known in itself in the art. The wavelength halving means may be provided for instance in internal mounting in the laser head, i.e. in the resonator, or in external mounting. The crystal may be fixedly mounted in position in the path of the laser beam, or it may be disposed to be movable into position e.g. electromechanically or with the aid of another operating means.

The laser head may also comprise an operating means for the wavelength halving means, for moving said halving means into the path of the laser beam.

When in the laser head of the invention e.g. an Nd:YAG laser source us used, the following wavelength combinations are obtainable. The main wavelength is about 1.06 μm, the next powerful output wavelength is about 1.32 μm; these wavelength ranges can be selected by means of respective different front and rear mirrors known themselves in the art, i.e. by replacing the front and rear mirrors.

Using the wavelength halving means, one obtains the second harmonic wavelengths: about 0.53 μm and 0.66μm. Such a 1.06–1.32–0.53–0.66μm Nd:YAG laser apparatus affords substantial advantages in certain fields of laser surgery, that is, the apparatus is appropriate for a variety of different uses. Moreover, the Nd:YAG laser source may be in continuous and/or pulse mode. Thus, four different wavelengths in continuous and/or pulse mode can be obtained with one laser source. When other laser sources emitting different wavelengths are used in the laser head, even a greater number of different wavelengths are obtained with the means, e.g. 8, 12 or more.

DETAILED DESCRIPTION OF THE INVENTION

Figure 1:
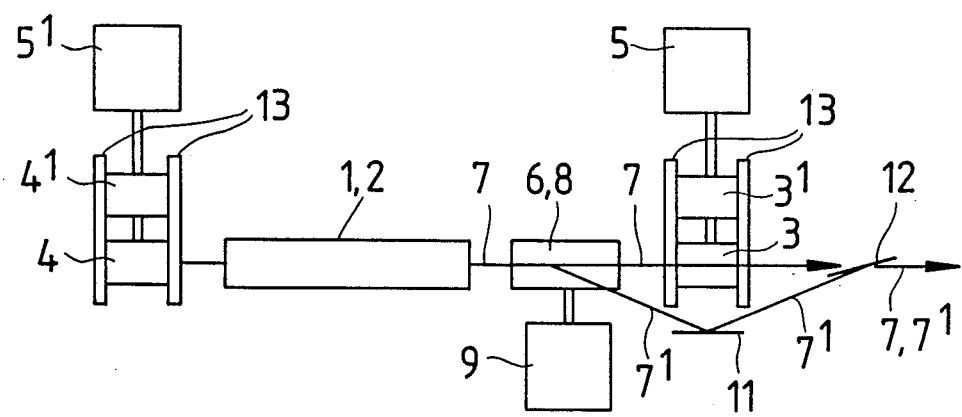
Figure 2:
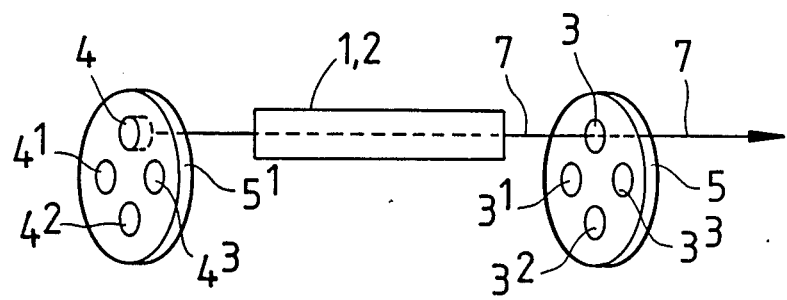
Figure 3:
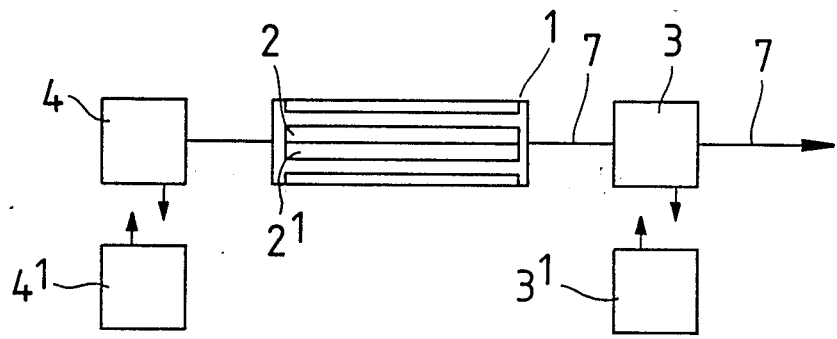

The invention is described in the following in detail with the aid of an embodiment example, referring to the drawing attached in which FIG. 1 presents, in elevational view and schematically, a laser head according to the invention, FIGS. 2 and 3 present, in elevational view and schematically, a second and a third laser head according to the invention.

The laser head according to the invention depicted in FIG. 1 comprises a laser resonator 1 comprising a laser crystal 2 and a front and a rear mirror 3, 4. The laser resonator including its crystal is of conventional type and will not be described more in detail in the present context. The laser resonator 1 has been disposed to provide a laser beam which is reflected, reinforced by the rear and front mirrors, through the front mirror; the path of the laser beam is indicated by reference numeral 7. As taught by the invention, the laser head comprises two pairs of front and rear mirrors 3, 4; $3^1$, $4^1$, which constitute two pairs differing in their dielectric laser light transmitting, respectively reflecting, properties in such manner that the first front and rear mirrors 3, 4 transmit, respectively reflect, laser light of a given wavelength $1_1$ (lambda=1), and the second front and rear mirrors $3^1$, $4^1$ transmit, respectively reflect, laser light of another given wavelength $1_2$. Furthermore, the first front and rear mirrors 3, 4 can be exchanged against the latter front and rear mirrors $3^1$, $4^1$. Thus, by exchanging the laser mirrors, two kinds of laser light of different wavelengths $1_1$, $1_2$ are selectively obtained from the laser head.

The laser head of FIG. 1 comprises operating means 5, $5^1$ for the front and rear mirrors, disposed to exchange the front and rear mirrors as described above. The operating means 5, $5^1$ may be electrical, hydraulic, pneumatic, or of any other type, e.g. shifting means with the aid of which the mirrors 3, $3^1$, respectively 4, $4^1$, movably carried on guides can be exchanged.

In the embodiment just described, the mirrors 3, $3^1$ and 4, $4^1$ have been arranged to be exchangeable mainly with the aid of a translatory movement on the guides 13.

The laser head depicted in FIG. 1 comprises furthermore a special wavelength halving means 6 placed in the path 7 of the laser beam for selecting the laser beam's wavelength. The halving means is proved with an operating means 9, such as an electrical, hydraulic or pneumatic shifting means for shifting the halving means, whenever desired, into and/or out of the path of the laser beam. The halving means consists e.g. of a KTP crystal (potassium titany phosphate, or KTi;OPO4, crystal), known in the art, with the aid of which, for instance, the halved wavelength ½ $1_1$, instead of the wavelength $1_1$ of mirrors 3, 4, is obtained from the laser head. Said halved wavelength, the path of the beam being indicated by reference numeral $7^1$, is partly reflected to one side from the crystal of the halving means 6 and it is further reflected with the aid of mirrors 11 and 12 to be conducted onto the path of the laser beam 7, e.g. in conventional manner with the aid of a mirror arm or equivalent guiding means to enter an optic fibre for further conduction to the object which is being operated on. When in the apparatus of FIG. 1 the second front and rear mirrors $3^1$, $4^1$are used, one obtains from the apparatus the wavelength $1_2$, and when the wavelength halving means 6 is employed, the wavelength ½ $1_2$.

In FIG. 2 is depicted a laser head of the type shown in FIG. 1, comprising a laser resonator 1 with laser source 2, and a front and a rear mirror 3, 4. Each of the mirrors 3, 4 has been placed in an operating means 5, $5_1$ of revolver type, rotatable about an axis paralleling the path 7 of the laser head. Each operating means 5, $5^1$ comprises several laser mirrors 3, $3^1$, $3^2$, $3^3$, respectively 4, $4^1$, $4^2$, $4^3$, which are similar, two and two, as to their dielectric laser light transmitting, respectively reflecting, properties in such manner that the front and rear mirror of each pair transmits, respectively reflects. Laser light of a given wavelength, which is different from that of any other mirror pair. In this way, it is possible to produce laser light of four different wavelengths with the apparatus.

The apparatus schematically depicted in FIG. 3 comprises a conventional laser resonator 1 with laser source 2, e.g. an Nd-YAG source, and with exchangeable front and rear mirrors 3, 4; $3^1$, $4^1$ disposed in the manner of the embodiment of FIG. 1. In addition, in the embodiment of FIG. 3, the laser resonator comprises a second laser source $2^1$, e.g. an Er-YAG source, in such manner that in the laser resonator either laser source, 2 or $2^1$, can be kept in operation as required, or using two power sources, both operating simultaneously. Each laser source emits laser light of the characteristic frequencies characteristic of the respective laser source, and by selecting appropriate mirrors, it is possible to shut out from the light that is produced the undesirable wavelengths; the desired wavelength, or wavelengths, is/are conducted to the desired object in a manner known in itself in the art.

The embodiment examples are merely intended to illustrate the invention, and the applications of the invention may vary within the scope of the claims stated below. For instance, one laser head may comprise e.g. several laser sources, several pairs of mutually consistent front and rear mirrors, potentially provided with operating means, and potentially with a wavelength halving means, and potentially provided with mirrors.

What I claim is:

1. A laser head comprising:
   (a) a first laser resonator having a laser source operable to produce a laser beam including light of different wavelengths;
   (b) a first pair of mirrors including one front mirror and one rear mirror;
      (i) said front mirror of said first pair of mirrors being adapted to selectively transmit therethrough laser light of a selected first wavelength;
      (ii) said rear mirror of said first pair of mirrors being adapted to selectively reflect laser light of said first selected wavelength toward said front mirror of said first pair of mirrors;
      (iii) said first pair of mirrors being selectively operably orientable in said laser beam;
   (c) a second pair of mirrors including one front mirror and one rear mirror;
      (i) said front mirror of said second pair of mirrors being adapted to selectively transmit therethrough laser light of a selected second wavelength;
      (ii) said rear mirror of said second pair of mirrors being adapted to selectively reflect laser light of said second selected wavelength toward said front mirror of said second pair of mirrors;
      (iii) said second pair of mirrors being selectively operably orientable in said laser beam; and,
   (d) means for selectively exchanging said first and second pairs of mirrors, for one another, to selectively orient only one pair of said first and second pairs of mirrors in said laser beam, at a time.

2. A laser head according to claim 1 including wavelength-halving means selectively positionable in said beam of laser energy.

3. A laser head according to claim 2, wherein said wavelength-halving means is a KTP, KDP, KD*P, ADP, or other equivalent crystal.

4. A laser head according to claim 1 including a second laser resonator operable to produce a laser beam including light of different wavelengths;
    (a) said first laser resonator comprising a Nd-YAG laser source;
    (b) said second laser resonator comprising an Er-YAG laser source; and,
    (c) both of said first an second laser sources being selectively alternatively positionable to produce a beam of energy directed between a selected pair of said first and second pairs of mirrors.

5. A laser head comprising:
    (a) a first laser resonator having a laser source operable to produce a laser beam including light of different wavelengths;
    (b) a first pair of mirrors including one front mirror and one rear mirror;
        (i) said front mirror of said first pair of mirrors being adapted to selectively transmit therethrough laser light of a selected first wavelength;
        (ii) said rear mirror of said first pair of mirrors being adapted to selectively reflect laser light of said first selected wavelength toward said front mirror of said first pair of mirrors;
        (iii) said first pair of mirrors being selectively operably orientable in said laser beam;
    (c) a second pair of mirrors including one front mirror and one rear mirror;
        (i) said front mirror of said second pair of mirrors being adapted to selectively transmit therethrough laser light of a selected second wavelength;
        (ii) said rear mirror of said second pair of mirrors being adapted to selectively reflect laser light of said second selected wavelength toward said front mirror of said second pair of mirrors;
        (iii) said second pair of mirrors being selectively operably orientable in said laser beam; and,
    (d) guide means in which said mirrors are mounted; and
    (e) means for selectively moving said guide means to exchange said first and second pairs of mirrors, for one another, to selectively orient only one pair of said first and second pair of mirrors in said laser beam, at a time.

* * * * *